United States Patent
Allen-Hoffmann (12) 
(10) Patent No.: US 6,514,711 B2
(45) Date of Patent: *Feb. 4, 2003

(54) IMMORTALIZED HUMAN KERATINOCYTE CELL LINE

(75) Inventor: B. Lynn Allen-Hoffmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/945,136

(22) Filed: Aug. 31, 2001

(65) Prior Publication Data

US 2002/0102726 A1 Aug. 1, 2002

Related U.S. Application Data (63) Continuation-in-part of application No. 09/769,124, filed on Jan. 24, 2001, which is a continuation of application No. 09/277,295, filed on Mar. 26, 1999, now Pat. No. 6,214,567, which is a continuation of application No. 09/114,557, filed on Jul. 13, 1998, now Pat. No. 5,989,837.

(51) Int. Cl.⁷ ......................... G01N 33/567; C12N 5/08
(52) U.S. Cl. ...................... 435/7.21; 435/347; 435/371; 435/373; 435/402; 435/408
(58) Field of Search ................................ 435/7.21, 347, 435/371, 373, 402, 408

(56) References Cited

U.S. PATENT DOCUMENTS 5,491,084 A    2/1996   Chalfie et al.
6,214,567 B1 * 4/2001   Allen-Hoffman et al. .. 435/7.21

OTHER PUBLICATIONS

L. Allen–Hoffman, et al., Proc. Nat'l. Acad. Sci. USA 81:7802–7806, 1984.

B.L. Allen–Hoffman, et al., "Use of RHEK–1 Immortalized Human Keratinocytes for Detection of Induced Mutation at the Hypoxanthine–guanine Phosphoriboxyltransferase Locus," Inter. J. Oncol. 3:619–625, 1993.

H.P. Baden, et al., "Isolation and Characterization of a Spontaneously Arising Long–lived Line of Human Keratinocytes (NM1)," In Vitro Cell. Dev. Biol. 23(3):205–213, 1987.

P. Boukamp, et al., "Cell Keratinization in a Spontaneously Immortalized Diploid Human Keratinocyte Cell Line," J. Cell Biol. 106:761–771, 1988.

J.A. Garlick and L.B. Tachman, "Fate of Human Keratinocytes During Reepithelialization in an Organotypic Culture Model," Lab. Invest. 70(6):916–924, 1994.

J.A. Garlick, et al., "Re–epithelialization of Human Oral Keratinocytes in vitro," J. Dent. Res. 75(3):912–918, 1996.

J.A. Garlick, "Skin Substitutes–Tissue Models for Cancer Biology," Bioengineering of Skin Substitutes, Sep. 18–19, Boston, MA, 1997.

C. Gilles, et al., "Immortalization of Human Cervical Keratinocytes by Human Papillomavirus Type 33," Int. J. Cancer 53:872–879, 1993.

M.A. Pickart, et al., "Development of an Organotypic Culture System for the Study of Human Squamous Cell Carcinoma," Proc. Am. Assoc. Canc. Res. 40:192, 1999 (Abstract).

R.H. Rice, et al., "Elevation of Cell Cycle Control Proteins During Spontaneous Immortalization of Human Keratinocytes," Mol. Biol. Cell 4:185–194, 1993.

D. Strickland, "Organogenesis gets Approval from FDA for Graftpatch; Stock Jumps 7 Percent," Bioworld Today 8(154):1–4, 1997.

* cited by examiner

*Primary Examiner*—Donna C. Wortman
(74) *Attorney, Agent, or Firm*—Quarles & Brady LLP (57) ABSTRACT

A method for testing the effects of various factors on human skin equivalent is disclosed. The method involves providing a human stratified squamous epithelial cell culture of an immortalized human keratinocyte cell line that forms a reconstructed epidermis, exposing the reconstructed epidermis to a factor and evaluating the effect of the factor on the reconstructed epidermis. A method for selecting preventive or therapeutic agents for skin damages caused by a factor using the same human stratified squamous epithelial cell culture system is also disclosed.

47 Claims, 3 Drawing Sheets

IMMORTALIZED HUMAN KERATINOCYTE CELL LINE

CROSS-REFERENCE TO RELATED APPLICATIONS

"This application is a CIP of U.S. Ser. No. 09/769,124 filed Jan. 24, 2001, which is a continuation of Ser. No. 09/277,295, filed Mar. 26, 1999, issued as U.S. Pat. No. 6,214,567, which is a continuation Ser. No. 09/114,557, filed Jul. 13, 1998, which has issued as U.S. Pat. No. 5,989,837."

STATEMENT REGARDING FEDERALLY SPONSORED RESEARCH OR DEVELOPMENT

This invention was made with United States government support awarded by the following agencies: NIH Grant No(s). AR40284, CA66786 and AR42853. The United States has certain rights in this invention.

BACKGROUND OF THE INVENTION

Skin is a continually renewing tissue that acts as one of the body's primary defense systems against environmental insult. Skin is composed of two layers, the dermis and the epidermis. The dermis, whose primary cellular components are fibroblasts, forms the foundation upon which the epidermis lies. Dermal fibroblasts, the primary cellular component of the dermis, exist in a sea of extracellular matrix. These matrix components not only physically support the overlying layers, but are also involved in biochemical signaling pathways. Clark, E. A. and J. S. Brugge, Science 268: 233–9 (1995). In addition to secreting matrix components, fibroblasts also secrete a spectrum of growth factors, which act on the overlying epidermis. Mass-Szabowski and N. E. Fusenig, J. Invest. Dermatol. 107: 849–55 (1996); Smola, H. et al., J. Cell Biol. 122: 417–29 (1993). The epidermis is a stratified squamous epithelium, composed primarily of keratinocytes. Keratinocytes within the epidermis are organized into four layers based on morphological and biochemical properties; these are the basal, spinous, granular, and cornified layers. Eckert, R. L. et al., Physiol Rev 77: 397–424 (1997). The basal layer rests atop the dermis and is in direct contact with the specialized extracellular matrix proteins of the basement membrane. Basal keratinocytes have the ability to replicate and are the source of all suprabasal keratinocytes within the epidermis. As basal cells divide, certain daughter cells lose contact with the basement membrane. These cells assume a suprabasal position and continue movement upward through the layers of the epidermis until they enucleate and are sloughed from the surface of the skin, a process known as terminal differentiation. The differentiation process in keratinocytes is accompanied by a pattern of characteristic changes in gene expression; a number of proteins serve as markers of terminal differentiation. Undifferentiated basal keratinocytes express the keratins K5 and K14 while differentiating cells express K1 and K10. Other proteins that are expressed in a specific pattern during keratinocyte terminal differentiation include precursors of the cornified envelope such as involucrin, filaggrin, pancornulin, cornifin, loricrin and elafin, as well as the cross-linking enzyme, epidermal transglutaminase. Morley, S. M. and E. B. Lane, The Keratinocyte Handbook, 293–321 (1994); Simon, M., The Keratinocyte Handbook, 275–292 (1994); Steinert, P. M. and L. N. Marekov, The Journal of Biological Chemistry 270: 17702–17711 (1995).

As one of the body's primary defense systems against environmental insult, skin often comes into contact with a wide spectrum of toxins, which may damage the skin. For example, human exposure to 2,3,7,8-tetrachlorodibenzo-p-dioxin (TCDD), one congener of a family of ubiquitous environmental toxins called dioxins, produces an array of clinical manifestations. Chloracne, a hyperkeratotic skin disorder, is the most consistently observed pathology in exposed humans. Historically, the effect of a toxin on human skin has been studied in vitro using monolayer culture systems. Human keratinocytes isolated from stratified squamous epitheliums can be readily cultivated in vitro. Leigh, I. M. and F. M. W., The Keratinocyte Handbook, 43–52 (1994). Cultivated keratinocytes replicate readily during early passage and can generate large numbers of cells which exhibit certain features of squamous differentiation in vivo. However, monolayer cultures of human keratinocytes do not form the epidermal tissue architecture that mimics a stratified squamous epithelium in human epidermis. Thus, studying a toxin's effects on human skin in monolayer keratinocyte cultures is flawed in that monolayer cultures do not reflect the normal in vivo tissue context. For example, although several laboratories have previously reported on the cellular responses of normal human or murine keratinocytes to TCDD in vitro, little evidence has been available to link these observations to the specific pathology observed in human skin.

When cultured normal human keratinocytes are transplanted onto mice, epidermal tissue architecture is regenerated over time in an orderly fashion. Breitkruetz, D. et al., Differentiation 61(3): 195–209 (1997). However, studying the effect of a toxin on human skin using transplanted animals can be time consuming and expensive. In addition, when primary human keratinocytes are used in monolayer cultures and transplanted animals, different batches of cells may vary one way or another, which further complicates the toxin testing process.

BRIEF SUMMARY OF THE INVENTION

In one embodiment, the present invention is a method for testing the effects of various factors on human skin equivalents. The method involves providing a human stratified squamous epithelial cell culture of an immortalized human keratinocyte cell line that forms a reconstructed epidermis, exposing the reconstructed epidermis to a test factor, and evaluating the effect of the factor on the reconstructed epidermis. Preferably, the culture further comprises a base layer of collagen and fibroblasts.

In a particularly advantageous embodiment of the invention, the spontaneously immortalized human keratinocytes are ATCC CRL 12191 cells. In another embodiment, the spontaneously immortalized human keratinocytes carry an exogenous gene, preferably green fluorescence protein gene.

In another preferred embodiment of the present invention, the factor is a material that may contact human skin or is selected from the group consisting of UV light, radiation, air pressure, environmental temperature, and friction.

In an preferred embodiment of the present invention, the effect of the factor on the reconstructed epidermis is selected from the group consisting of cell differentiation, cell proliferation, cell survival, cell damage, and cell death. In another embodiment, the effect may be selected from the group consisting of tissue culture morphology change, barrier function, and tissue strength.

Another embodiment of the present invention is a method for selecting preventive or therapeutic agents for skin damages caused by a test factor. The method involves providing a human stratified squamous epithelial cell culture of an immortalized human keratinocyte cell line that forms a reconstructed epidermis, exposing the reconstructed epidermis to a factor that can cause damage in the reconstructed epidermis, exposing the reconstructed epidermis to an agent being screened for preventive or therapeutic use, and evaluating the effect of the agent on the reconstructed epidermis.

In a preferred embodiment of the present invention, the exposure of the reconstructed epidermis to the factor may occur prior to, after, or at the same time as the exposure of the reconstructed epidermis to the agent being screened for production of a therapeutic use.

In separate embodiments of the invention, the test factors described above in various embodiments may be in liquid, solid, emulsion, gaseous, or solvent form. The agent to be screened may also be in solvent, liquid, solid, gaseous, or emulsion form.

It is an advantage of the present invention that the effects of a factor on a tissue culture system mimics the effects of the factor on human skin in vivo.

Further objects, features and advantages of the invention will be apparent from the following detailed description when taken in conjunction with the accompanying claims and drawings.

DETAILED DESCRIPTION OF THE INVENTION

In the examples described below, a spontaneously immortalized human keratinocyte cell line has been obtained and characterized. Culturing the spontaneously immortalized human keratinocyte cell line using an organotypic culturing system has been shown to produce a three dimensional architecture of keratinocytes similar to human epidermis. When tested for effects of toxins using TCDD as an example, the organotypic culture of the immortalized human keratinocytes demonstrated similar lesions as those observed in TCDD-exposed human skin.

One embodiment of the present invention is a method for testing the effects of various factors on human skin equivalent. The method involves providing an organotypic culture of an immortalized human keratinocyte cell line, exposing the organotypic culture to a test factor, and evaluating the effect of the factor on the organotypic culture. "In the examples below, one immortalized cell line and one method of organotypic culture that can be used as human skin equivalent in the present invention are shown. Other immortalized human keratinocyte cell lines and other organotypic culture methods may also be used as long as the organotypically cultured human keratinocyte cell lines can form an architecture that mimics the human skin epidermis. Whether an organotypic culture of a cell line can do so can easily be determined by one of ordinary skill in the art as described in the examples below. It is understood that spontaneously immortalized human keratinocytes containing a heterologous transgene, such as a marker gene, may also used in the present invention. In the examples shown below, the ATCC CRL-12191 cells were transfected with a green fluorescence protein gene and the transfected cells have been shown to be able to form an architecture that mimics human skin epidermis in organotypic culture. ATCC CRL 12191 was deposited at the American Type Culture Collection, 10801 University Boulevard, Manassas, Va., on Sep. 20, 1996, under the terms and conditions of the Budapest Treaty. The inclusion of a marker transgene in the cells may also help to follow cellular metabolic change.

The inclusion of a marker transgene in the cells may help to unambiguously identify human keratinocytes' response to exogenous compounds and/or treatments. Constructs composed of transgenes, such as GFP, luciferase, and other commonly used biological readouts, and containing inducible promoter(s) which are activated by various treatments and/or exposure to agents may result in a highly sensitive, quantitative, and tissue-specific human skin testing assay. Examples of inducible promoters of interest are those that regulate transcription of drug metabolizing enzymes (cytochrome P450 superfamily), stress response genes, differentiation-responsive genes, genes that regulate growth control (growth factor, cytokines, growth factor receptors), genes that regulate programmed cell death.

In a preferred method, one would expose the test factor to a human stratified squamous epithelial cell culture as described below in the Examples. In a more generalized preferred method, one would obtain an immortalized human stratified squamous epithelial cell culture capable of forming a reconstructed epidermis and identify a test factor. The test factor may be in a variety of forms, preferably solid, liquid, emulsion, gaseous, or combined with a solvent. One would combine the cell culture and the test factor and evaluate the effect of the factor on the reconstructed epidermis.

A very wide range of factors including anything that may come into contact with human skin can be tested for their effects on human skin using an organotypic culture of a spontaneously immortalized human keratinocyte cell line. In one embodiment of the present invention, the test factor is a material that may contact human skin. The material may be a chemical compound or a mixture of compounds. Examples of the suitable compound or mixture of compounds include, but are not limited to, inorganic acids, organic acids, acid mixtures, acid derivatives, amines, inorganic bases, organic bases, base mixtures, a mixture of an acid and a base, cleaners, detergents, surfactants, and industrial chemicals. The test factor may be a toxin in the environment, something being considered to be used in a variety of products such as therapeutics, cosmeceuticals and cosmetic skin products, or these products themselves.

The factor may also be, but is not limited to, an environmental condition such as UV light, radiation, air pressure, environment temperature, or friction. The factor may have a beneficial or a damaging effect on human skin.

A wide range of effects of the test factor on human skin may be evaluated. Example of the effects that may be evaluated include but are not limited to cell differentiation, cell proliferation, cell survival, cell damage, cell death, morphology change such as that of different cells and layers of an organotypic culture, barrier function, and tissue strength. Barrier function in the permeability barrier and water loss barrier created by the lamellar granules used withe the plasma membrane of a granular cell. The lamellar granules secrete their contents into the intracellular spaces. These granules contain neutral sugars linked to lipids and or proteins; hydrolytic enzymes, possibly responsible for degrading intracellular material; and free steroids. The action of enzymes such as steroid sulfatase, removes the lipids from the upper stratum corneum and brings about desquamation of the cells there. This is important for the quality of skin and also allows this organ to rid itself of cells that are damaged, contain bacteria or viruses, or are detrimental.

Barrier function can be evaluated in several ways: (1) Surface electrical capacitance using a NOVA Dermnaphase impedance meter, (2) determination of lipid composition (extract lipids from skin samples and resolve lipid species by thin layer chromatography, specific classes of lipids, particularly certain ceramides, correlate with a mature epidermal barrier), and (3) ultrastructure analysis (electron microscopy to visualize presence or absence of alternating electron-dense and translucent lipid lamellae between corneocytes (squames). When they also evaluate any DNA ray data that could be generated. This would allow one to identify new genes in human keratinocytes or enable one to identify known genes that are affected (positively or negatively) by a test compound.

Some of these effects are related to and/or overlap each other and may occur at the same time. Depending on the purpose of a test, one or more of the above effects mentioned above, and other effects not mentioned, above may be evaluated. For example, if the purpose of a test is to determine toxicity or damage to human skin by a tested compound, cell viability and cell membrane damage may be used as the measured effects. The term toxicity and the term damage are used exchangeably to refer to any negative change in human skin or organotypic culture from a normal stratified squamous epithelium.

If the purpose of a test is to find a compound that can be used in a cosmetic product that will slow down skin cell growth and differentiation, then cell growth and differentiation may be the effects evaluated. One of ordinary skill in the art is familiar with the methods that can be used to evaluate an effect. For example, for cell survival and cell membrane damage evaluation, MTT cell viability assay and lactate dehydrogenase assay may be performed, respectively. For cell differentiation evaluation, cell morphology and changed distribution of differentiation-specific protein marker may be analyzed. For cell replication and growth evaluation, BrdU assay may be performed.

Another embodiment of the present invention is a method for selecting preventive or therapeutic agents for skin damages caused by a factor. The method involves providing an organotypic culture of an immortalized human keratinocyte cell line, exposing the organotypic culture to the factor that can cause damage in the organotypic culture, exposing the organotypic culture to an agent being screened for preventive or therapeutic use, and evaluating the effect of the agent on the organotypic culture. For selecting therapeutic agents, exposing the organotypic culture to the factor that can cause damage in the organotypic culture may occur prior to exposing the organotypic culture to an agent being screened for therapeutic use or the two exposures may occur at the same time. For selecting preventive agents, exposing the organotypic culture to the factor that can cause damage in the organotypic culture may occur after exposing the organotypic culture to an agent being screened for preventive use or the two exposures may occur at the same time. The effects of an agent on the organotypic culture being evaluated is whether the damage on the organotypic culture from the factor is reduced partially, completely or did not occur at all. The agent may be a compound or mixture of compounds or may be an environmental condition such as UV light, radiation, air pressure, environmental temperature, or friction.

In another embodiment, the present invention is a method of evaluating the effects of a plurality of compounds on a human skin equivalent comprising the steps of providing a plurality of cell cultures comprising spontaneously immortalized human keratinocytes and a set of test compounds, sequentially exposing the plurality of cell cultures to the set of compounds, either alone or in combination, and evaluating the effects of the compounds on the cell cultures. Preferably, the cell cultures are provided in a format of either 24-well plates or 40- or 96-well plates. In another embodiment of the present invention, the set of compounds is a combinatorial library of compounds. The spontaneously immortalized human keratinocytes may comprise a reporter gene or exogenous gene, preferably GFP.

EXAMPLE 1

Normal Growth and Differentiation in a Spontaneously Immortalized Near-Diploid Human Keratinocyte Cell Line, BC-1-Ep/SL (NIKS™ Cells)

A. Materials and Methods

1. Cell Culture

Normal keratinocytes (BC-1-Ep) were isolated from newborn human foreskin. Keratinocyte cultures were established by plating aliquots of a single cell suspension in the presence of mitomycin C-treated Swiss mouse 3T3 fibroblasts. Allen-Hoffman, B. L. and J. G. Rheinwald, *PNAS USA* 81: 7802–7806 (1984). The standard keratinocyte culture medium was composed of a mixture of Ham's F12:Dulbecco's modified Eagle's medium (DME), (3:1, 0.66 mM calcium) supplemented with 2.5% fetal calf serum (FCS), 0.4 µg/ml hydrocortisone (HC), 8.4 ng/ml cholera toxin (CT), 5 µg/ml insulin (Ins), 24 µg/ml adenine (Ade), 10 ng/ml epidermal growth factor (EGF), 100 units penicillin and 100 µg/ml streptomycin (P/S). The cells were passaged at weekly intervals at $3 \times 10^5$ cells on a 100 mm$^2$ tissue culture dish with feeders. Transformed cells, BC-1-Ep/SL (spontaneous line), appeared at passage 16. BC-1-Ep/SL cells at passage 55 tested negative for mycoplasma (Wisconsin State Laboratory of Hygiene, Madison, Wis.). Recombinant human EGF obtained from R+D Systems. Transforming growth factor beta (TGF-β) was purified from human platelets.

2. Chromosomal Analysis

Cells in log phase growth were arrested in metaphase with 50 ng/ml colcemid, then trypsinized and pipetted from the flask for centrifugation. After removal of the media and trypsin, the cells were suspended in a hypotonic 75 mM KCl solution for 20 minutes, fixed with 3:1 methanol/acetic acid three times and dropped onto glass slides. Slides were aged two weeks, lightly trypsinized and stained with Giemsa (Seabright, 1971). In each sample, the chromosomal identities and abberations were determined in well-spread G-banded metaphases by photographic analysis and the cutting of at least two karyotypes for band to band comparison of chromosomal homologs.

3. DNA Fingerprinting

DNA was isolated from keratinocytes using Qiagen QIAamp Blood Kit (Qiagen, Inc., Santa Clarita, Calif.). DNA fingerprint analysis used the GenePrint Fluorescent STR System according to protocols recommended by manufacturer. The twelve primer pairs are divided into three quadriplexes (CTTv, FFFL, and GammaSTR). Each quadriplex was amplified in separate reactions using 25 ng of DNA as template. Amplification was preformed in a Perkin-Elmer 9700 thermal cycler (Perkin-Elmer, Corp., Norwalk, Conn.). PCR products were electrophoresed on 42 cm×33 cm×0.4 mm polyacrylamide gels in a BRL sequencing apparatus (Life Technologies, Inc., Gaithersburg, Md.). Gels were then scanned on a Hitachi FMBIO II Fluorescent Scanner.

4. Growth of BC-1-Ep/SL Cells in Athymic Mice

BC-1-Ep/SL cells were injected into nude athymic mice to determine if they could form tumors. A suspension of $5 \times 10^6$ cells in 100 µl Ham's F12 was injected subcutaneously into the flanks of six nude mice. As a negative control, the parental BC-1-Ep 6° cells were injected at $3 \times 10^6$ cells /100 µl F12. As a positive control, SCC4 cells were injected at $3 \times 10^6$/100 µl F12. Mice were weighed and tumors measured 26 days later.

5. Suspension in Semi-solid Media

For suspension studies, preconfluent cultures were removed from culture dishes with 0.5 mM EDTA, 0.1% trypsin and washed in serum-containing medium to inactivate any residual trypsin. After a short centrifugation (440×g for 3 minutes), cells were resuspended at $1 \times 10^6$ cells/ml in 3 parts Ham's F-12 plus 1 part DME made semi-solid with 1.68% methylcellulose (4,000 centipoises, Fisher Scientific, Fairlawn, N.J.) as described in Sadek and Allen-Hoffmann, 199. Sadek, C. M. and B. L. Allen-Hoffman, *J. Biol. Chem.* 269:16067–16074 (1994). Cells were recovered from suspension by repeated dilution with serum-free medium and centrifugation (440×g for 10 minutes). Following one rinse with phosphate-buffered saline (0.137 M NaCl; 2.7 mM KCl; 8.1 mM Na$_2$HPO$_4$; 1.4 mM KH$_2$PO$_4$; pH 7.2) (PBS), cells were either resuspended in PBS (pH 7.2) to assay for CE formation or lysed in SLS buffer (50 mM Tris; 10 mM EDTA, pH 8.0; 0.5% (w/v) sodium lauroyl sarcosine) to determine DNA fragmentation. Control controls consisted of adherent keratinocytes treated for similar times in 3 parts Ham's F-12 plus 1 part DME.

6. Northern Analysis

Cells were grown in standard keratinocyte culture medium on a 3T3 feeder layer. The feeder layer was removed 24 hours prior to RNA isolation with 0.02% EDTA in PBS. Poly A$^+$ RNA was isolated from logarithmically growing cells as previously described. Sadek, C. M. and B. L. Allen-Hoffman, *J. Biol. Chem.* 269: 16067–16074 (1994). Poly A$^+$ RNA was electrophoresed in a 1.2% agarose gel containing formaldehyde and electroblotted to a Zeta-probe membrane (Bio-Rad Laboratories, Richmond, Calif.). The membrane was prehybridized and then hybridized in the presence of a random primer [$^{32}$P]-dCTP-labeled cDNA probe as recommended by the supplier. The cDNA probes used for detection include rat glyceraldehyde-3-phosphate dehydrogenase, pGPDN5, monkey TGF-β1, EGF receptor, mouse keratin 14 (gift from Dennis Roop), TGF-α, and a 830-bp 5' fragment of human c-myc. Fort, P. et al., *Nucl. Acids Res.* 13: 1431–1442 (1985); Sharples, K. et al., *DNA* 6: 239–244 (1987); Xu, Y. et al., *Nature* 309: 806–810 (1984); Kudlow, J. E. et al., *J. Biol. Chem.* 264: 3880–3883 (1989); Miyamoto, C. et al., *Proc. Natl. Acad. Sci. USA* 82: 7232–7236 (1985).

7. Cornified Envelope (CE) Formation

Keratinocytes were removed from culture plates and recovered from suspension as described previously. Cells from each treatment were counted and resuspended in triplicate at $10^6$ cells/ml in PBS (pH 7.2) containing 1% SDS and 20 mM dithiothreitol. Samples were boiled for 5 minutes in a waterbath and cooled to room temperature. DNase (0.5 µg/ml) was added and CEs counted using a hemacytometer. CE formation was calculated as a percentage of input cells.

8. Analysis of Nucleosomal DNA Fragmentation

DNA was isolated and labeled as previously described. Sachsenmeier, K. F. et al., *J. Biol. Chem.* 271: 5–8 (1996). Briefly, $2.5 \times 10^6$ cells were lysed in 500 µl of 50 mM Tris, 10 mM EDTA pH 8.0 and 0.5% (w/v) sodium lauroyl sarcosine. The lysate was extracted with phenol:chloroform:isoamyl alcohol (25:24:1, v:v:v) and ethanol precipitated. The DNA was dissolved in 20 µl TE buffer, pH 8.0, and quantitated by absorption at 260 nm. Intact and fragmented DNA was 3' end-labeled with [$\alpha^{32}$P]-ddATP using terminal dideoxynucleotidylexotransferase. Tilly, J. L. and A. J. Hsueh, *J. Cell Physiol.* 154(3): 519–26 (1993). One half of each labeled sample was loaded onto a 1.5% agarose gel and electrophoresed. Gels were dried with heat using an SE 1200 Easy Breeze (Hoefer Scientific, San Francisco, Calif.) and exposed to Kodak Biomax MR film.

9. Formation of Organotypic Cultures

Organotypic cultures were grown as previously described. Parenteau, N., *Keratinocyte Methods* (1994). A collagen raft was formed by mixing normal human neonatal fibroblasts, CI-1-F, with Type I collagen in 10% FCS+F12+penicillin/streptomycin. Rafts were allowed to contract for 5 days. The parent cells, BC-1-Ep (5°) and the BC-1-Ep/SL (38°) cells were plated on the rafts at $3.5 \times 10^5$ cells in 50 µl 0.2% FCS+3F12:1DME+HC+Ade+Ins+CT+P/S containing 1.88 mM calcium. Cells were allowed to attach 2 hours before adding an additional 13 mls of media (Day 0). On Day 1 and 2 cells were refed. On Day 4, cells were lifted to the air interface with cotton pads and switched to cornification medium (2% FCS+3F12:1DME+HC+Ade+Ins+CT+P/S containing 1.88 mM calcium). Cells were fed cornification medium every three days. On Day 15 rafts were fixed with freshly made modified Karnovsky's fixative consisting of 3% glutaraldehyde and 1% paraformaldehyde in 0.1 M cacodylate buffer, pH 7.4, at room temperature for 3 hours. Before removing the culture media, fixative was gently added to the cells on top of the raft to prevent cornified layers from floating away. Subsequently, the culture media was aspirated and the culture wells filled with fixative. The raft was cut in half with one half processed for light microscopy and the other half for electron microscopy.

10. Tissue Sectioning

Fixed rafts were embedded in paraffin, sectioned and stained with hematoxylin and eosin by Surgical Pathology, University Hospital, Madison, Wis. Stained sections were viewed and photographed using an Olympus IX-70 microscope equipped with a 35 mm camera.

11. Electron Microscopy

Fixed cultures were washed 3 times with 0.1 M cacodylate buffer, pH 7.4. Under a dissecting microscope, a scalpel was used to detach the polyester mesh supporting the raft culture from the plastic insert. The raft was cut with a scalpel into approximately 2 mm×4 mm pieces which were stored overnight in buffer. Following postfixation with 1% osmium tetroxide at 4° C., the keratinocytes were washed 4 times, 15 minutes each, with 0.1 M maleic acid, pH 6.5, before en bloc staining with 2% aqueous uranyl acetate for 1 hour. After washing with distilled water, keratinocytes were dehydrated with increasing concentrations of ethanol, 100% propylene oxide, and infiltrated with 1:1 propylene oxide:eponate overnight. Rafts were embedded in fresh Eponate in flat embedding molds and oriented so they could be sectioned perpendicularly on a Reichert Ultracut E3 ultramicrotome equipped with diamond knife. Thin sections were stained with lead citrate and examined in a Hitachi H-7000 electron microscope (Hitachi, San Jose, Calif.) operated at 75 kV.

12. Transfection Cell Culture

For transfection experiments, BC-1-Ep/SL cells were plated at a density of $3 \times 10^5$ cells onto mitomycin C-treated Swiss mouse 3T3 fibroblasts in 100 mm dishes. Cells were given 48 hours to adhere at which time the 3T3 layer was removed with 0.5 mM EDTA. Cells were rinsed twice with DME and serum-containing media was added. Cells were transfected 24 hours later.

13. Plasmid DNA

Plasmid DNA was prepared with the Endotoxin Free Maxiprep Kit (Qiagen). pGreenLantern was linearized using XmnI. pcDNA3 neo and pTracer-SV40 (Invitrogen) were linearized using BglII (Promega). Expression of green fluorescent protein (GFP) is driven by a constitutively active CMV promoter in both pGreenLantern and pTracer-SV40 plasmids.

14. Determination of Optimal Conditions for Transfection of BC-1-Ep/SL Cells

BC-1-Ep/SL cells passage 30°–40° were transfected using the polycationic lipid GeneFECTOR (VennNova). The transfection mix is made by adding 20–33 $\mu$g linearized plasmid DNA to 500 $\mu$l sterile milli-Q water for each 100 mm dish. Different amounts of GeneFECTOR were added depending on the ratio of total DNA to GeneFECTOR which varied from 1:2 to 1:4. The transfection mix was swirled gently and incubated for 15 minutes at room temperature. Media was removed from the BC-1-Ep/SL cells, plates were rinsed twice with DME and refed with 5 mls of DME. The transfection mix was added to each plate in a drop-wise fashion and cells were incubated for 5 hours at 37° C. under 5% $CO_2$. The medium was removed and cells were rinsed twice with DME and refed with serum-containing media. The cells were viewed 24 hours post-transfection with an IX-70 inverted fluorescent microscope (Olympus) equipped with a GFP short band pass filter to check for successful transfection before analysis or flow activated cell sorting (FACS).

15. Optimal Transient Transfection Efficiency

BC-1-Ep/SL cells passage 30°–40° were transfected using the polycationic lipid GeneFECTOR (VennNova). The transfection mix was made by adding 15 $\mu$g linearized pGreenLantern and 5 $\mu$g pcDNA3neo (20 $\mu$g total DNA) to 500 $\mu$l sterile milliQ water for each 100 mm plate of cells. Genefector is then added at a quantity of three times that of the total DNA (1:3 ratio of DNA to GeneFECTOR). The transfection mix was swirled gently and incubated for 15 minutes at room temperature. Media was removed from the BC-1-Ep/SL cells, plates were rinsed twice with DME and refed with 5 mls of DME. The transfection mix was added to each plate in a dropwise fashion and cells were incubated for 5 hours at 37° C. under 5% $CO_2$. The medium was removed and cells were rinsed twice with DME and refed with keratinocyte media. The cells were viewed as described previously.

16. Flow Cytometry

Twenty-four hours post-transfection, BC-1-Ep/SL cells were removed from culture with 0.5 mM EDTA and 0.1% trypsin. After short centrifugation (440×g for 5 minutes), cells were resuspended in serum-containing medium at $2 \times 10^6$ cells/ml. 500 $\mu$l of this cell suspension was filtered through 42 $\mu$m mesh (Tetko, Inc.) and stained with 5 $\mu$g/ml propidium iodide (PI) immediately prior to analysis. Transfected BC-1-Ep/SL cells were analyzed on either a FACScan or FACSCalibur benchtop flow cytometer (both from Becton Dickinson) equipped with a laser tuned to 488 nm. Ten thousand events were acquired and analyzed using CellQuest software (Becton Dickinson) and analysis was restricted to live events only, based on PI staining. Cell viability and transient transfection efficiency data were obtained.

17. Cell Sorting

We used the following protocol to obtain stable GFP-expressing BC-1-Ep/SL cells. Twenty-four hours post-transfection, cells were removed using 0.5 mM EDTA and 0.1% trypsin. After short centrifugation (440×g for 5 minutes), cells were resuspended in serum-containing medium at a density of $5-7 \times 10^6$ cells/ml. This suspension was then filtered through 42 $\mu$m sterile mesh (Tetko, Inc.). Immediately prior to sorting, cells were stained with 5 $\mu$g/ml propidium iodide. Transfected BC-1-Ep/SL cells were sorted on a FACStar Plus (Becton Dickinson) equipped with a coherent argon laser tuned to 488 nm. Transfection efficiency data was obtained with CellQuest software (Becton Dickinson). Cells were sorted at a rate of 2000/second and samples were collected post-sort to check viability and GFP expression.

18. Colony Forming Efficiency

Colony forming efficiencies (CFE) were obtained by plating 1000 events onto duplicate 60 mm plates in the presence of mitomycin C-treated Swiss mouse 3T3 fibroblasts. After one week, plates were fixed for 10 minutes in 10% formalin, rinsed with tap water, and stained overnight with methylene blue. Colonies were counted and divided by the number of events plated to obtain the final CFE. Based on the CFE calculated, the total number of colonies formed was obtained by multiplying the number of events by the CFE. GFP-expressing colonies were counted 10–12 days post-sorting using an IX-70 inverted fluorescent microscope with a GFP short band pass filter. The number of GFP-expressing colonies was divided by the total number of colonies formed to obtain a stable GFP expressing colony forming efficiency.

19. Isolation and Identification of Stable pGreenLantern Transfected BC-1-Ep/SL cells BC-1-Ep/SL cells were transfected with pGreenLantern as described previously and sorted based on fluorescence. Immediately following cell sorting, GFP-positive BC-1-Ep/SL cells were reinitiated into culture. Cells were plated at low density from $2-3\times10^4$ cells per 100 mm dish onto mitomycin C-treated Swiss mouse 3T3 fibroblasts. Cells were monitored every other day using an IX-70 inverted fluorescent microscope (Olympus) with a GFP short band pass filter. Non-GFP expressing colonies were removed by scraping and stable GFP expressing colonies were allowed to expand. When GFP expressing colonies had grown to an estimated density of 1000 cells or more, they were isolated by ring cloning and replating onto 60 mm plates with ring mitomycin C-treated 3T3's and expanded.

20. Isolation and Identification of Stable pTracer-SV40 Transfected BC-1-Ep/SL cells BC-1-Ep/SL cells were transfected using 20 μg of pTracer-SV40 and a 1:4 ratio of DNA to GeneFECTOR (VennNova). Twenty-four hours post-transfection cells were removed with 0.5 mM EDTA, 0.1% trypsin and resuspended at a density of $2\times10^6$ cells/ml in serum containing medium. Three $\times10^6$ cells were replated onto two 100 mm plates with a mitomycin C-treated Swiss mouse 3T3 fibroblasts. Forty-eight hours after passage, GFP-positive cells were selected for 5 days with 250 μg/ml zeocin (Invitrogen). Stable GFP-expressing BC-1-Ep/SL cells were purified using sterile cell sorting and expanded as described previously.

21. Histological Analysis of Transfected Organotypic Cultures

GFP-expressing BC-1-Ep/SL cells at 43° passage were plated at a density of $3\times10^5$ cells/collagen raft and grown in organotypic culture for 16 days. Raft cultures were fixed for at least one hour in 4% paraformaldehyde before embedding in paraffin. Five μm sections were cut and alternate sections were stained with hemotoxylin and eosin (H&E) by Surgical Pathology, UW-Madison. Non-H&E sections were rehydrated, stained with 5 μg/ml Hoechst dye (33258) for 15 minutes, dehydrated and mounted using Cytoseal mounting media (Stephens Scientific). Sections were viewed and photographed using an IX-70 inverted fluorescent microscope (Olympus) equipped with a dual FITC-Hoechst filter.

22. Analysis of GFP Expression by Confocal Microscopy

GFP-expressing BC-1-Ep/SL cells at 43° passage were plated at a density of $3\times10^5$ cells/collagen raft and grown in organotypic culture for 16 days. Raft cultures were fixed overnight in 4% paraformaldehyde-PBS and rinsed for one hour in a 0.1 M glycine-PBS solution at 4° C. Whole rafts were mounted, coverslipped using Vectashield mounting media (Vector labs) and sealed with rubber cement. GFP expression was analyzed using a confocal laser scanning microscope (Nikon Diaphot 200) with excitation at 488 nm and detection at 500–530 nm bandpass filter. Images were taken at 10 μm intervals starting at the upper cornified layer. The microscope is located in the W. M. Keck Neural Imaging Laboratory, University of Wisconsin-Madison.

B. Results

1. Isolation of the BC-1-Ep/SL Cell Line

Cells were desegregated from a neonatal foreskin by trypsinization. Keratinocytes were initiated into culture by plating an aliquot of the cell suspension onto a mitomycin C-treated Swiss mouse 3T3 feeder layer in standard keratinocyte growth medium containing 0.66 mM calcium. Fibroblasts were initiated into culture by plating an aliquot of cell suspension onto a tissue culture plate containing Ham's F-12 medium supplemented with 10% fetal calf serum.

After approximately 9 days, primary cultures of keratinocytes designated strain BC-1-Ep were cryopreserved and subcultured onto a feeder layer. Fibroblast cultures were grown to near confluency and also cryopreserved. In early passages, the BC-1-Ep cells exhibited no morphological or growth characteristics that were atypical for cultured normal human keratinocytes. Cultivated BC-1-Ep cells exhibited stratification as well as features of programmed cell death.

To determine replicative lifespan, the BC-1-Ep cells were serially cultivated to senescence in standard keratinocyte growth medium at a density of $3\times10^5$ cells per 100 mm dish. By passage 15 most keratinocytes in the population appeared senescent as judged by the presence of numerous abortive colonies which exhibited large, flat cells.

However, at passage 16, keratinocytes exhibiting a small cell size were evident. By passage 17, only the small sized keratinocytes were present in the culture and no large, senescent keratinocytes were evident. The resulting population of small keratinocytes that survived crisis appeared morphologically uniform and produced colonies of keratinocytes exhibiting typical keratinocyte characteristics including cell-cell adhesion and apparent squame production.

The keratinocytes that survived senescence were serially cultivated at a density of $3\times10^5$ per 100 mm dish for 59 passages, demonstrating that the cells had achieved immortality. The keratinocytes which emerged from the original senescencing population are termed BC-1-Ep/spontaneous line (BC-1-Ep/SL).

2. Cytogenetic Analysis and DNA Fingerprinting

Figure 1:
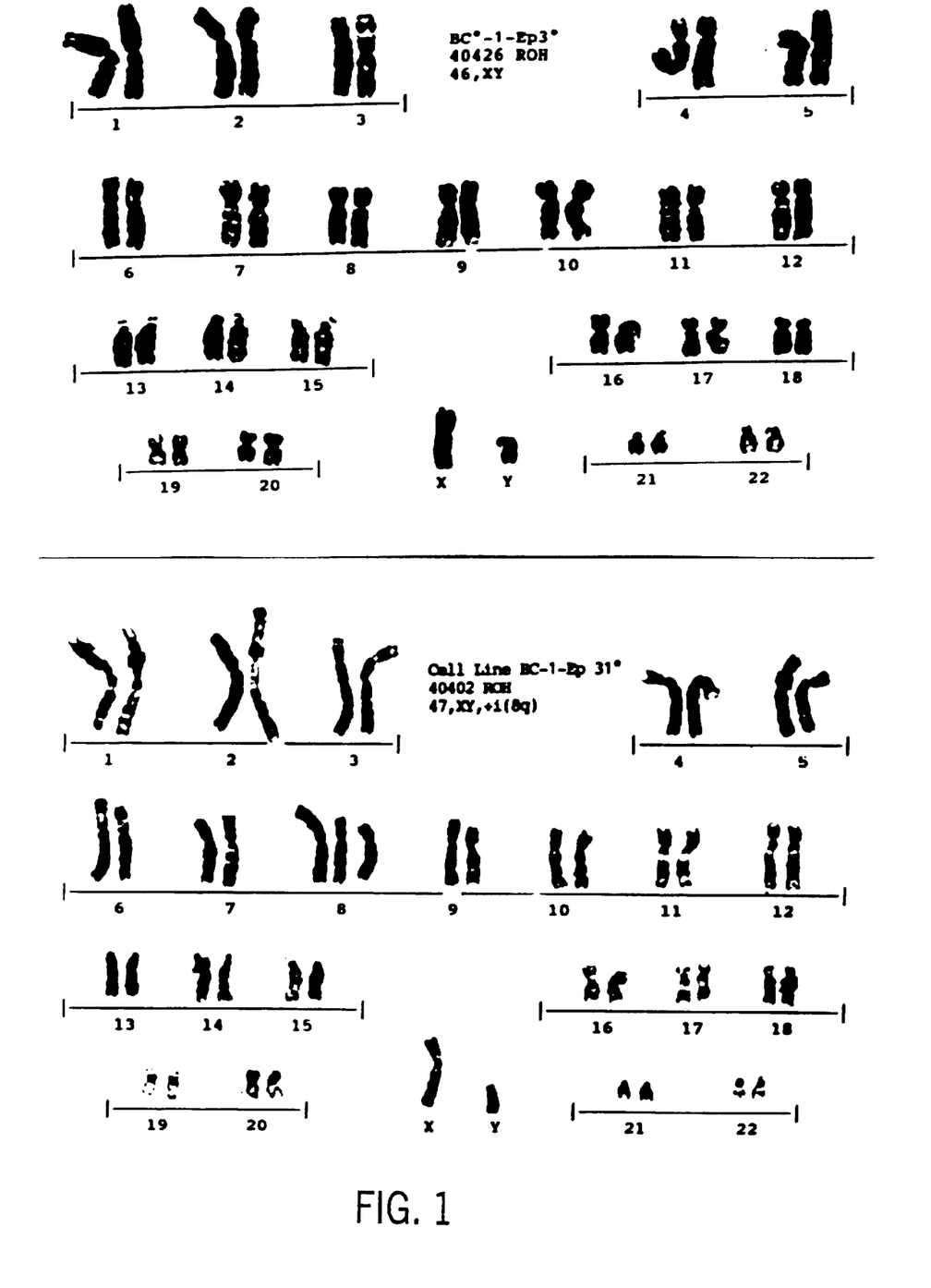
FIG. 1 is a chromosomal analysis of BC-1-Ep/SL cells (NIKS™ cells). Karyotypic analysis was performed on BC-1-Ep/SL cells at passage 31. The cells contained 47 chromosomes due to an extra isochromosome of the long arm of chromosome 8. The extra chromosome, i(8q), is not seen in the parental keratinocytes (BC-1-Ep passage 3) which exhibited a normal male karyotype.

Chromosomal analysis was conducted on the parental BC-1-Ep cells at passage 3 and BC-1-Ep/SL cells at passages 31 and 54. The parental BC-1-Ep cells have a normal chromosomal complement of 46, XY. At passage 31 all BC-1-Ep/SL cells contained 47 chromosomes due to an extra isochromosome of the long arm of chromosome 8 (FIG. 1). No other gross chromosomal abnormalities or marker chromosomes were detected. At passage 54 all cells contained the isochromosome 8, however, an additional isochromosome of the long arm of chromosome 1 and a marker chromosome were present in a small fraction of the population (Table 1 in Appendix 1). The BC-1-Ep/SL cells have been screened for the presence of proviral HIV DNA sequences and found to be negative. Regions of the HIV provirus were amplified enzymatically, hybridized to radio-labelled HIV-1 specific DNA probes, and the amplified DNA separated by size and visualized using agarose gel electrophoresis and autoradiography. Polymerase chain reaction products were compared by size and specificity to known HIV-1 positive and negative controls. The presence of HPV16, and 31 viral sequences were assessed by Southern analysis and none were detected.

The DNA fingerprints for the BC-1-Ep/SL cell line and the BC-1-Ep keratinocytes are identical at all twelve loci. The odds of the BC-1-Ep/SL cell line having the parental BC-1-Ep DNA fingerprint by random chance is $4\times10^{16}$. The DNA fingerprints for ED-1-Ep, SCC4 and SCC13y are different from the BC-1-Ep pattern. The data from our DNA fingerprint analysis of the BC-1-Ep/SL cell line proves it arose from the parental BC-1-Ep cells. This data also shows that keratinocytes isolated from other humans, ED-1-Ep, SCC4, and SCC13y, are unrelated to the BC-1-Ep cells or each other. The BC-1-Ep/SL DNA fingerprint data provides an unequivocal way to identify the BC-1-Ep/SL cell line.

3. BC-1-Ep/SL Keratinocytes are Not Tumorigenic in Athymic Nude Mice

To determine the tumorigenicity of the parental BC-1-Ep keratinocytes and the immortal BC-1-Ep/SL keratinocyte cell line, cells were injected into the flanks of athymic nude mice. The human squamous cell carcinoma cell line, SCC 4, was used as a positive control for tumor production in nude mice. The injection of samples was designed such that each animal received an injection of SCC 4 cells in one flank and either the parental BC-1-Ep keratinocytes or the BC-1-Ep/SL cells in the opposite flank. This injection strategy eliminated animal to animal variation in tumor production and confirmed that the mice would support vigorous growth of tumorigenic cells. Neither the parental BC-1-Ep keratinocytes (passage 6) nor the BC-1-Ep/SL keratinocytes (passage 35) produced tumors in nude mice. The results of the tumorigenicity testing is shown in Table 2 in Appendix 1.

4. Growth Characteristics in vitro

BC-1-Ep/SL keratinocytes are nontumorigenic and exhibit morphological characteristics of normal human keratinocytes when cultured in standard keratinocyte growth medium in the presence of mitomycin C-treated 3T3 feeder cells. To further evaluate the growth characteristics of the BC-1-Ep/SL cells, we examined the steady state mRNA levels of known autocrine regulators of keratinocyte growth. Northern analysis of mRNAs from the BC-1-Ep/SL cell line revealed that expression of autocrine growth factors, such as transforming growth factor-$\alpha$ (TGF-$\alpha$) and transforming growth factor-$\beta$ (TGF-$\beta$), as well as the levels of epidermal growth factor receptor (EGFR) and c-myc, are similar, if not identical, to the parental BC-1-Ep keratinocytes.

Figure 2:
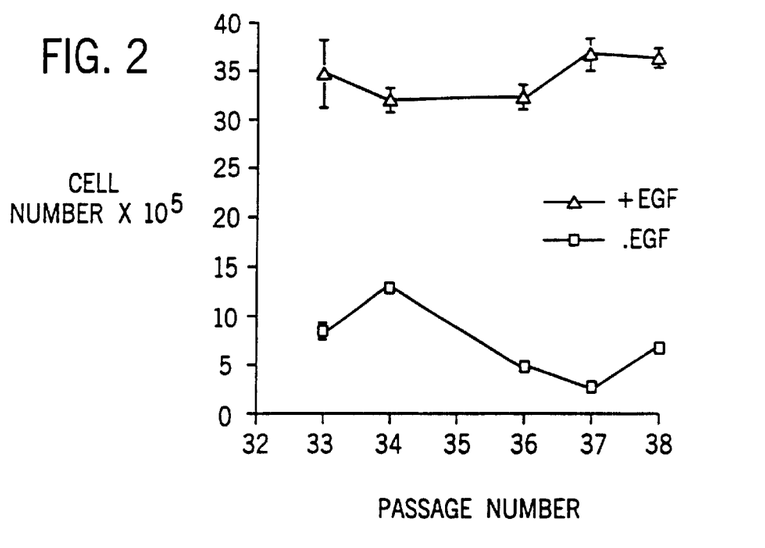
FIG. 2 demonstrates the requirement for epidermal growth factor (EGF) for serial passage of BC-1-Ep/SL cells. BC-1-Ep/SL cells were serially passaged in standard media ±10 ng/ml EGF. The cells survived without EGF but grew poorly.

We next determined which constituents of standard keratinocyte growth medium are required for optimal growth of BC-1-Ep/SL cells. Serial cultivation in the absence of epidermal growth factor (EGF) resulted in a 60 to 90% reduction in cell number at each passage, compared to EGF-containing control cultures (FIG. 2). The dependence on EGF for growth of BC-1-Ep/SL cells appears to be a stable characteristic. BC-1-Ep/SL cells at passage 50 continue to exhibit a dependence on EGF for optimal growth.

Figure 3:
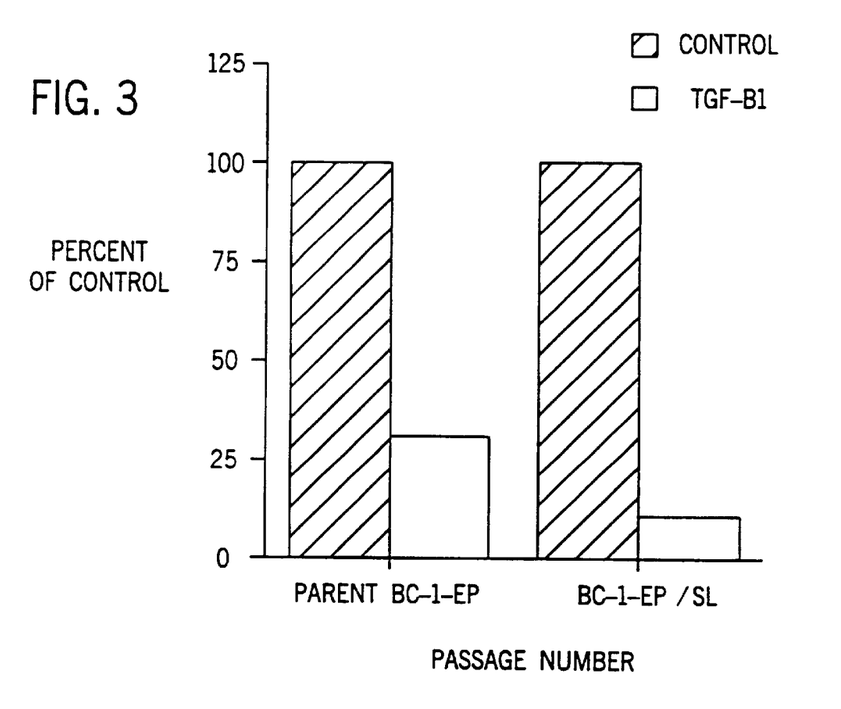
FIG. 3 demonstrates that transforming growth factor-β-1 (TGF-β1) inhibits growth of BC-1-Ep/SL keratinocytes. The parent cells, BC-1-Ep (6°) and BC-1-Ep/SL (28°) were plated in standard media without EGF or a 3T3 feeder layer. Cells were treated ±5 ng/ml TGFβ1 when the cells were ~20% confluent in standard media without EGF. Cells were counted 3–5 days later. The effect of TGF-β1 treatment is shown as a percentage of controls.

Another polypeptide growth factor that plays an important role in epidermal homeostasis is transforming growth factor-$\beta$1 (TGF-$\beta$1). In vitro, TGF-$\beta$1 is an inhibitor of growth in cultured normal human keratinocytes (Pientenpol, et al., 1990), however malignant transformation of keratinocytes often results in attenuation of TGF-$\beta$1-induced growth inhibition (Bascom, et al., 1989; Parkinson, et al., 1983; Pietenpol, et al., 1990; Rice, et al., 1992). Like the normal parental BC-1-Ep keratinocytes, TGF-$\beta$1 inhibits the growth of the BC-1-Ep/SL cell line (FIG. 3). The TGF-$\beta$1-induced growth inhibition is reversible in both the parental and BC-1-Ep/SL keratinocytes.

Figure 4:
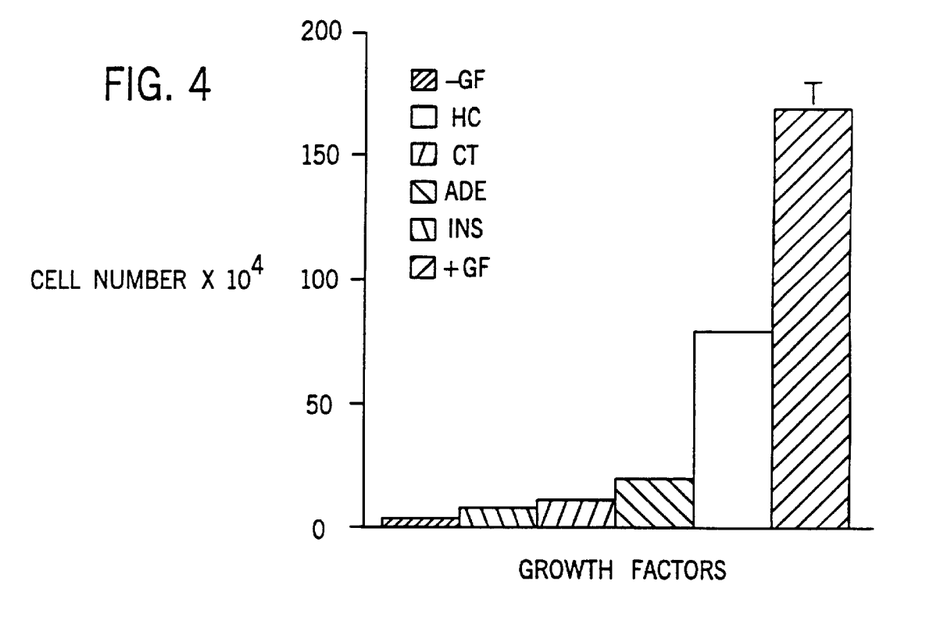
FIG. 4 demonstrates growth factor requirements of BC-1-Ep/SL cells. BC-1-Ep/SL cells at passage 31 were grown in 2.5% FCS+3F12:1DME+10 ng/ml EGF supplemented with no additional growth factors (−GF), 0.4 $\mu$g/ml hydrocortisone (HC), 8.4 ng/ml cholera toxin (CT), 24 $\mu$g/ml adenine (Ade), 5 $\mu$g/ml insulin (Ins), or all growth factors (+GF). Cell growth increased in the presence of each growth factor alone, however optimal growth was achieved in the presence of all growth factors.

To further characterize the requirements for optimal in vitro growth of the BC-1-Ep/SL keratinocytes, cultures were cultivated in medium supplemented with 2.5% fetal calf serum, EGF, and individual constituents of the standard growth medium. FIG. 4 demonstrates that addition of insulin alone promotes a 15-fold increase in cell number. However, addition of all constituents of standard keratinocyte growth medium promotes a 30-fold increase in BC-1-Ep/SL cell number. These findings demonstrate that the BC-1-Ep/SL cell line has maintained cell type-specific requirements for growth in vitro.

5. Differentiation Characteristics in vitro

We next investigated whether BC-1-Ep/SL cells could undergo normal differentiation in both surface culture and organotypic culture. We monitored a marker of squamous differentiation, the formation of cornified envelopes (CE). In cultured human keratinocytes, early stages of CE assembly result in the formation of an immature cornified envelope composed of involucrin, cystatin-a and other proteins, which represent the innermost third of the mature cornified envelope. We examined CE formation in the parental cells and the BC-1-Ep/SL keratinocytes (Table 3 in Appendix 1). Less than two percent of the keratinocytes from either the adherent parental cells or the BC-1-Ep/SL cell line produce CE's. This finding is consistent with our previous studies demonstrating that actively growing, subconfluent keratinocytes produce less than five percent CE. Hines, M. D. et al., *J. Biol. Chem.* 271: 6245-6251 (1996). To determine whether the BC-1-Ep/SL cell line is capable of producing CE's when induced to differentiate, the cells are removed from surface culture and placed in suspension for 24 hours in medium made semi-solid with methylcellulose. Many aspects of terminal differentiation, including differential expression of keratins and CE formation can be triggered in vitro by loss of keratinocyte cell-cell and cell-substratum adhesion. Drosdoff, V. and W. J. Pledger, *J. Cell. Biol.* 123: 909–919 (1993); Green, H., *Cell* 11: 405–416 (1977). We found that the BC-1-Ep/SL keratinocytes produced as many and usually more CE's than the parental keratinocytes (Table 3 in Appendix 1). These findings demonstrate that the BC-1-Ep/SL keratinocytes are not defective in their ability to make this cell type-specific differentiation structure.

6. BC-1-Ep/SL cells undergo apoptosis following loss of adhesion

We next determined whether BC-1-Ep/SL keratinocytes undergo apoptosis by assaying nucleosomal cleavage of DNA. Specific DNA cleavage into oligonucleosomal fragments is a hallmark of apoptosis. Arends, M. J. et al., *Am J Pathol.* 136(3): 593–608 (1990); Wyllie, A. H., *Nature* 284(5756): 555–6 (1980). Keratinocytes from all species studied to date can undergo apoptosis both in vivo and in vitro. Epidermal keratinocytes are destined to enucleate and lose metabolic activity as part of their differentiation pathway. Many parallels exist between keratinocyte terminal differentiation and apoptosis. We assessed the ability of the parental and BC-1-Ep/SL keratinocytes to undergo nucleosomal cleavage following suspension. Normal cultured human keratinocytes exhibit both morphological and biochemical features of apoptosis when deprived of cell-cell and cell-substrata contact by suspension in semi-solid medium. Adherent, preconfluent keratinocytes from parental or BC-1-Ep/SL cell line grown in serum-free, additive-free medium for 24 hours exhibited no detectable DNA fragmentation. Similarly, adherent cells treated for an identical time with semi-solid, serum-free, additive-free medium did not exhibit nucleosomal fragmentation. When suspended in semi-solid medium both the parental and BC-1-Ep/SL keratinocytes exhibited DNA fragmentation. These findings are consistent with previous studies from our laboratory demonstrating that normal human keratinocytes induced to differentiate by loss of adhesion will fragment their DNA. Hines, M. D. et al., *J. Biol Chem.* 271: 6245–6251(1996); Sachsenmeier, K. F. et al., *J. Biol. Chem.* 271: 5–8 (1996). Taken together, these data demonstrate that the BC-1-Ep/SL keratinocytes are capable of differentiating and respond normally to cell type-specific signals to undergo apoptosis.

7. Organotypic cultures of BC-1-Ep/SL cells exhibit normal squamous differentiation To confirm that the BC-1-Ep/SL keratinocytes can undergo normal squamous differentiation, the cells were cultivated in organotypic culture. Differentiation of keratinocytes cultured on a plastic substrata under medium promotes growth and limited differentiation. Specifically, human keratinocytes become confluent, stratify and produce a multilayered sheet that is similar to stratified epithelium. However, by light and electron microscopy there are striking differences between the architecture of the multilayered sheets formed in tissue culture and intact human skin. Organotypic culture is a technique to culture keratinocytes under in vivo-like conditions. Specifically, the cells adhere to a physiological substrata, fibrillar collagen embedded with dermal fibroblasts, and are lifted to the air-medium interface so that the cells can grow with their upper sheets air-exposed and with the proliferating basal cells closest to the gradient of nutrients provided by diffusion through the collagen gel. Under these conditions, correct tissue architecture is formed.

We compared both the parental cells, BC-1-Ep 50°, and the cell line, BC-1-Ep/SL 38°, grown in organotypic culture. Several characteristics of a normal differentiating epidermis are evident. In both the parental cells and the BC-1-Ep/SL cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the BC-1-Ep parental cells and the BC-1-Ep/SL cells. The appearance of flattened squamous cells is evident in upper layers of keratinocytes located above the basal layer and demonstrates that stratification has occurred. In the uppermost part of the tissue, the enucleated squames are shown peeling off the top of the culture. To date, we have not observed any histological differences in differentiation at the light microscope level between the parental BC-1-Ep keratinocytes, and BC-1-Ep/SL keratinocyte cell line grown in organotypic culture.

To confirm our histological observations, BC-1-Ep 6° and BC-1-Ep/SL 38° were analyzed using electron microscopy. Higher magnification allowed us to observe more detailed characteristic structures of normal differentiation in the raft cultures. Examination of micrographs convinced us that BC-1-Ep/SL cells undergo normal stratification in organotypic culture. This was similar to what was seen with the parental BC-1-Ep cells. We also noted the formation of hemidesmosomes in the basal layer, which also suggests that the cell line is able to form structures found in normal human epidermis. Hemidesmosomes are specialized structures which increase adhesion of the keratinocytes to the basal lamina and help maintain the integrity and strength of the tissue. Both the light level and electron microscopy data demonstrate that the BC-1-Ep/SL cell line can stratify and differentiate normally in organotypic culture.

8. Optimal transient transfection efficiency of the BC-1-Ep/SL cell line

We have chosen to use the plasmid, pGreenLantern, which contains the gene for green fluorescent protein (GFP) as a marker of transfection. GFP is a naturally fluorescing, non-toxic protein form jellyfish which is easily seen when exposed to UV light. In addition, some experiments included co-transfection of pGreenLantern with another plasmid, pcDNA3neo, which contains a gene for neomycin resistance allowing cells to grow in the presence of G 418. However, use of G418 as a selection method can be extremely toxic to keratinocytes and may inadvertently kill positively transfected cells. We believe that sterily sorting cells based on GFP expression will provide a quick way to select for positive transfectants and is the least toxic selection method available at present.

There have been many parameters to consider in optimization of transfection in this system. We have narrowed these down to the three most essential for obtaining the maximum transfection efficiency. These parameters include cell confluence, total amount of DNA (concentration) and the ratio of DNA to transfection reagent (GeneFECTOR). Transfections are completed using set parameters and cells are analyzed the following day with an inverted fluorescent microscope for presence of GFP expression. In addition, flow cytometry is used to obtain information on the viability and number of GFP positive cells.

Figure 5:
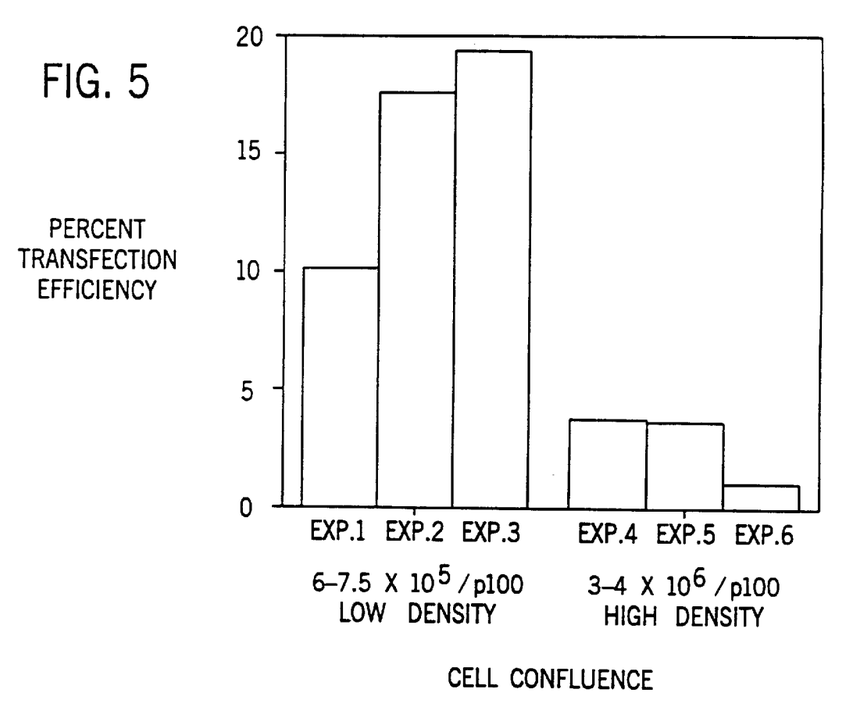
FIG. 5 shows that increased cell confluence reduces transient transfection efficiency in BC-1-Ep/SL cells. BC-1-Ep/SL cell were transfected with the GFP containing plasmid pGreenLantern (Gibco) and pcDNA3 neo (Invitrogen) using GeneFECTOR (VennNova Inc.). A range of 15–20 $\mu$g of linearized pGreenLantern and 5–6.7 $\mu$g of pcDNA3neo was used. Cell numbers were obtained by trypsinization and counting of keratinocytes using a hemacytometer. Low density was defined as 6–7.5×$10^5$ cells/100 mm dish. High density was defined as 3–4×$10^6$ cells/100 mm dish. Transfection efficiency was obtained using fluorescence activated cell sorting (FACS). Each bar of the graph represents a single experiment.

Cell confluence appears to be critical in obtaining the maximum transfection efficiency. BC-1-Ep/SL cells at varying levels of confluence were transfected with a range of 20–25 $\mu$g of DNA and analyzed 24 hours later by flow cytometry. Transient transfection efficiencies from several experiments suggest that a low confluence of $5-7\times10^5$ cells/100 mm dish (~30% confluent) will yield the highest transfection efficiency ranging from 10–19.5%. Transfections completed at high confluence, $2-4\times10^6$ cells/100 mm dish (~70% confluent), yielded much lower transient transfection efficiencies of 1–3% (FIG. 5).

Optimal DNA concentration was also tested using total amounts of pGreenLantern and pcDNA3neo ranging from 20–33 $\mu$g. All other parameters were held constant. We found that higher levels of total DNA do not yield better transfection efficiency. Our data suggest that a total 20 $\mu$g of DNA is optimal for the transfection of BC-1-Ep/SL cells, resulting in a transient transfection range of 3.79–13.64% (Table 4 in Appendix 1) (Cell confluence is included in this table to account for variability in transfection efficiency between experiments). We observed by flow cytometry that higher amounts of DNA caused increased toxicity to the cells.

The third parameter examined in optimizing transfection efficiency of BC-1-Ep/SL cells was the ratio of DNA to transfection reagent. Several different ratios of DNA to GeneFECTOR were investigated, these include 1:2, 1:3, and 1:4. Transient transfection efficiencies collected from triplicate experiments indicate that a ratio of one part DNA to three parts GeneFECTOR (1:3) is optimal, with transfection efficiencies ranging from 10–19.5% (Table 5 in Appendix 1) (Cell confluence is included to account for variability in transfection efficiency between experiments). We have concluded that a cell confluence of 30% ($5-7\times10^5$ cells/100 mm dish), total of 20 $\mu$g DNA, and a 1:3 ratio of DNA to GeneFECTOR are the conditions for optimal transient transfection efficiency in the BC-1-Ep/SL cell line.

9. Identification and isolation of stable GFP transfected BC-1-Ep/SL cells

Using the optimized conditions for transient transfection efficiency, we have successfully isolated and obtained stable GFP-expressing BC-1-Ep/SL cells. Stable expression is defined by integration of the GFP gene into the host cell's chromosomes. From earlier observations of transiently transfected GFP positive cells, there was concern that the brightest cells, those with the highest GFP expression, may be too differentiated to maintain colony forming ability when replated in surface culture. To test this, cells were transfected and sterily sorted based on the fluorescent intensity of GFP expression from dimmest to brightest. GFP positive cells acquired from cell sorting were plated and stable colonies detected and counted 10–12 days post-sort. Variability of GFP expression in these colonies was noted. The larger differentiated cells appear to have brighter GFP expression. The stable, GFP positive colony forming efficiency (CFE) was calculated as described previously. Three separate cell sorting experiments have been completed and the percentage of stable GFP positive cells was calculated to be 3.2%, 4.7%, and 5.64%. A sample table which represents one of these experiments is shown (Table 6 in Appendix 1). Data obtained in triplicate experiments suggest those cells with the greatest GFP fluorescence appear to have lower colony forming efficiency than less GFP fluorescent cells. The GFP positive CFE will allow us to estimate the number of GFP positive cells that need to be plated in order to obtain a reasonable number of stably transfected colonies.

As a result of the sterile sorts, we were able to isolate and expand several clonal lines of stable GFP expressing BC-1-Ep/SL cells. Lines expressing GFP from both pTracer-SV40 and pGreenLantern vectors have been serially passaged with no apparent changes in cell morphology or decrease in GFP expression.

10. Stable transfectants of BC-1-Ep/SL keratinocytes expressing green fluorescent protein exhibit normal stratification in organotypic culture To test the ability of the stably transfected GFP positive BC-1-Ep/SL cells to recreate normal tissue architecture, we plated these cells into organotypic culture. This type of culture allows the cells to display as many characteristics of intact skin as possible in a three dimensional microenvironment. This procedure has been repeated in triplicate and the resulting tissue analyzed histologically by fluorescent microscopy as well as confocal microscopy (data not shown). It appears that the stably transfected cells differentiate similarly to an untransfected BC-1-Ep/SL control. Both cultures show comparable cell stratification with no noticeable histological differences at the light microscope level. Interestingly, the appearance of GFP is most intense in the differentiated upper layers of the culture. We have observed this expression pattern with both fluorescent and confocal microscopy. The differences in GFP intensity maybe the result of variations in the amount of protein accumulated in the cell layers. Alternatively, the CMV promoter driving GFP expression may not become active until the cell reaches a more differentiated state.

EXAMPLE 2

The Effect of TCDD on Keratinocytes in Organotypic Culture

A. Materials and Methods

1. Cell Treatments

TCDD (Wellington Laboratories, Guelph, Ontario, Canada) was prepared in dimethylsulfoxide (DMSO) such that the final concentration of DMSO in the treatment medium did not exceed 0.1%. The final concentration of TCDD in the culturing medium was $10^{-8}$ M. Solvent controls included 0.1% DMSO.

2. Organotypic Culture

Modification in the three-dimensional organotypic culture of keratinocytes have been previously described. Parenteau, N. L. et al., *Cytotechnology* 9: 163–171 (1992); Allen-Hoffmann, BL et al., *J. Invest. Dermatol.*, 114 (3): 444–55 (2000). In the modified method, a dermal equivalent was formed by mixing normal human neonatal fibroblasts with type I collagen (Organogenesis, Canton, Mass.) in Ham's F-12 supplemented with 10% Fetal Clone 11 (HyClone, Logan, Utah) and 100 units penicillin and 100 µg/ml streptomycin (P/S). The gel was allowed to contract before 300,000 NIKS cells were plated onto the collagen base. After two hours, plating media was added and cultures were treated in the media with either TCDD or DMSO. Plating media is a mixture of Ham's F12: Dulbecco's modified Eagle's medium (3:1, 1.88 mM calcium) supplemented with 0.2% Fetal Clone II, 0.4 µg/ml hydrocortisone, -8.4 ng/ml cholera toxin, 5 mg/ml insulin, 24 mg/ml adenine, and 1% P/S. On day 4, cultures were lifted to the air interface with sterile cotton pads and switched to cornification media. Cornification media is a mixture of Ham's F12: Dulbecco's modified Eagle's medium (3:1, 1.88 mM calcium) supplemented with 0.2% Fetal Clone II, 0.4 µg/ml hydrocortisone, 8.4 ng/ml cholera toxin, 5 mg/ml insulin, 24 mg/ml adenine, and 1% P/S. Cultures were retreated at each media change. For proliferation assays, 5-bromo-2'-deoxyuridine (BrdU) (Sigma, St. Louis, Mo.) was added to culture media at a final concentration of 10 µM for 8 hours prior to harvesting.

At 8 days post-plating, cultures were either cryopreserved or fixed and paraffin embedded. Paraffin-embedded samples were fixed overnight in 4% paraformaldehyde/PBS, embedded in paraffin, and sectioned by the Pathology Department Histology Laboratory (University of Wisconsin-Madison, Madison, Wis.). For cryopreserved samples tissue was fixed for 2 hours with 1% paraformaldehyde/PBS and stored in 20% sucrose/PBS overnight at 4° C. in preparation for freezing. The tissue was then frozen in OCT media in liquid-chilled isopentane stored at -20° C. and mounted on charged glass slides. Some paraffin-embedded sections were stained with hematoxylin and eosin for evaluation of culture morphology. Stained sections were viewed and video images captured using an Olympus IX-70 microscope.

3. Electron Microscopy

Fixed organotypic cultures were washed 3 times with 0.1 M cacodylate buffer, pH 7.4. Under a dissecting microscope, a scalpel was used to detach the polyester mesh supporting the organotypic culture from the plastic insert. The organotypic culture was cut with a scalpel into approximately 2 mm×4 mm pieces, which were stored overnight in 0.1 M cacodylate buffer, pH 7.4. Following postfixation with 1% osmium tetroxide at 4° C., the organotypic cultures were washed 4 times, 15 minutes each, with 0.1 M maleic acid, pH 6.5, before en bloc staining with 2% aqueous uranyl acetate for 1 hour. After washing with distilled water, organotypic cultures were dehydrated with increasing concentrations of ethanol, 100% propylene oxide, and infiltrated with 1:1 propylene oxide:Eponate overnight. Organotypic cultures were embedded in fresh Eponate in flat embedding molds and oriented so they could be sectioned perpendicularly on a Reichert Ultracut E3 ultramicrotome equipped with a diamond knife. Thin sections were stained with lead citrate and examined in a Hitachi H-7000 electron microscope (Hitachi, San Jose, Calif.) operated at 75 kV.

4. Immunohistochemical Analysis of Organotypic Cultures

Primary antibodies used were anti-transglutaminase-1 and anti-filaggrin (Biomedical Technologies Inc., Stoughton, Mass.), anti-keratin-1 (Novo Castra, Newcastle upon Tyne, UK), anti-involucrin, and anti-active caspase-3 ® and D Systems, Minneapolis, Minn.). For filaggrin, and keratin-1 immunohistochemistry, paraffin-embedded organotypic cultures were serially sectioned (5 µm), mounted on glass slides and deparaffinized in xylene followed by an ethanol series. Sheibani, N. and B.L.A.-H., *Keratinocyte Methods*, 167–174 (1994). For transglutaminase-1 and involucrin immunohistochemistry cryopreserved samples were sectioned, mounted on glass slides and fixed for 5 minutes in ice cold acetone. Sections to be stained with keratin-1 and filaggrin were microwaved in 10 mM sodium citrate pH 6.0 for 3.5 minutes to promote antigen exposure. All sections were washed with PBS and blocked with 3% normal goat serum (Sigma, St. Louis, Mo.) in PBS. Sections were incubated with primary antibody (1:100 anti-transglutaminase-1 for 1 hour at 37° C.; 1:25 anti-filaggrin for 1 hour at room temperature; 1:20 anti-keratin-1 for 1 hour at room temperature; 1:1000 anti-involucrin for 1 hour at room temperature; 1:50 anti-active caspse-3 overnight at 37° C.). Sections were then incubated with secondary antibodies, a 1:500 dilution of Alexa 594-conjugated goat anti-rabbit IgG (for involucrin and active caspase-3) or Alexa 488-conjugated goat anti-mouse IgG (for all others) (Molecular Probes, Eugene Oreg.). All sections were counterstained with 5 µg/ml Hoechst 33258. Samples were viewed with an IX-70 inverted fluorescence microscope (Olympus) equipped with FITC (470 nm±20), Hoechst (525 nm±20), and Texas Red (360±20) band pass filters.

BrdU labeled cultures were sectioned (5 µm), deparaffinized, and microwaved in 10 mM sodium citrate pH 6.0 for antigen exposure. Sections were rinsed in PBS and peroxidase-quenched with 1:9 30% $H_2O_2$: MeOH for 10 minutes. Sections were then treated with 2N HCl for 20 minutes. After blocking with 5% normal goat serum/PBS, sections were incubated with anti-BrdU antibody (Becton Dickinson, San Jose, Calif.) for 3 hours at room temperature. A biotinylated horse anti-mouse IgG was used, followed by the Vectastain Elite ABC reagent kit (Vector Laboratories, Burlingame, Calif.). Bound enzyme-linked biotin was detected with 3,3'-diaminobenzidine tetrahydrochloride (Sigma, St. Louis, Mo.) and 0.003% $H_2O_2$/TBS.

5. In situ 3' End Labelling of Organotypic Culures

Free 3' ends of DNA were detected in sections of organotypic cultures (5 µm) using the APOPTAG Fluorescein In Situ Apoptosis Detection kit (Intergen). Sections were deparaffinized and protein digested with 20 µg/ml proteinase K for 15 minutes in water. Terminal deoxynucleotidal transferase (TdT) in sample buffer was applied. Samples were covered with plastic coverslips and incubated for 1 hour at 37° C. Slides were placed in 37° C. stop buffer for 30 minutes. Anti-digoxin fluor was applied in block buffer. Samples were covered with plastic coverslips and incubated 1 hour at 37° C. Samples were counterstained with Hoechst 33258. Sections were viewed with an IX-70 inverted fluorescence microscope (Olympus) equipped with FITC (470 nm±20) and Hoechst (525 nm±20) band pass filters.

B. Results

1. TCDD Causes Accelerated Onset of Terminal Differentiation in Organotypic Culture Organotypic co-culture of human keratinocytes and dermal fibroblasts provides a powerful in vitro system in which to investigate TCDD-induced dermatopathology. Unlike monolayer culture of keratinocytes, which has traditionally been employed to explore the effects of TCDD on human skin, organotypic culture recapitulates the three-dimensional tissue microenvironment of skin and accounts for epithelial-mesenchymal interactions. Studies in both humans and rodents have indicated heavy involvement of the dermis in the TCDD-induced dermatopathology, chloracne. Caputo, R. et al., *J. Am. Acad. Dermatol.* 19: 812–9 (1988); Moses, M. and P. G. Prioleau, *J. Am. Acad. Dermatol.* 12: 497-506 (1985); Panteleyev, A. A. et al., *J. Invest. Dermatol.* 108: 330–5 (1997); Poland, A. and J. C. Knutson, *Annu. Rev. Pharmacol. Toxicol.* 22: 517–54 (1982). For example, in addition to epidermal hyperplasia, hair follicle abnormalities and dermal cyst formation are cited as hallmarks of chloracne. Therefore, any critical examination of the effects of TCDD on skin should account for both dermal and, epidermal compartments. The system described here provides a novel method to explore the impact of TCDD on stratified squamous epithelium, which reveals the full spectrum of TCDD's effects on human skin.

NIKS cells were grown in organotypic culture in the presence of DMSO or TCDD fro 8 days. Cultures were then fixed, paraffin embedded, sectioned, and stained with hematoxylin and eosin. Organotypic cultures of keratinocytes treated with TCDD in the medium show changes in morphology and differentiation characteristics as compared to vehicle controls. At eight days post-plating, TCDD-treated organotypic cultures possess a well-developed cornified layer which is absent in time-matched controls. This effect was also observed in organotypic cultures of primary human keratinocytes, verifying that NIKS cells in organotypic culture respond to TCDD in a manner identical to that observed in primary human keratinocytes. Analysis of TCDD-treated cultures using electron microscopy at 11 days post-plating reveals definitive signs of accelerated differentiation. In the immediately suprabasal layers of control samples, keratinocytes are only beginning to flatten, whereas these same cells in TCDD-treated cultures display the flattened appearance of more mature keratinocytes. Furthermore, TCDD-treated samples exhibit a layer of keratinized tissue far more extensive than that observed in vehicle control cultures. Measurements taken from the electron micrographs show that the ratio of the thickness of the keratinized to non-keratinized layers is significantly greater in the TCDD-treated cultures (Table 7). This increased ratio can be attributed to both an increase in the amount of keratinized material and a flattening of the non-keratinized spinous layer in the TCDD-treated cultures. These observations are important not only because the organotypic culturing system provides a model in which the effect of TCDD on skin can be studied in vitro, but also because the effect produced in the model resembles the hyperkeratotic characteristics of chloracne in intact human skin.

2. TCDD Causes Aberrant Expression of Differentiation-specific Protein Markers

In addition to observing gross morphological changes in the TCDD-treated organotypic cultures, we also assessed whether the cultures displayed any abnormalities in expression of differentiation-specific protein markers. Organotypic cultures of both primary human keratinocytes and NIKS cells faithfully support patterns of differentiation marker expression nearly identical to those of intact skin. TCDD-treated and vehicle (DMSO) control rafts were harvested 8 days post-seeding and immunohistochemistry was performed to examine the expression and spatial distribution of involucrin, filaggrin, transglutaminase-1 and keratin 1. All markers examined were present in both TCDD-treated and control cultures. However, the pattern of differentiation marker expression was aberrant in TCDD-treated cultures. The expression pattern of filaggrin, an intermediate filament—associated protein, is most dramatically altered by TCDD treatment. Control samples exhibit characteristically punctate, but evenly distributed, staining in the granular layer. In contrast, filaggrin expression was evident in cellular layers more proximal to the basal layer in TCDD-treated samples than in control samples. Furthermore, filaggrin expression in TCDD-treated samples was patchy within the granular layer, with areas of very bright staining and areas of very faint staining, as opposed to the even distribution observed in control sections. These two observations suggest that TCDD interferes with the regulation of both the temporal and spatial expression of filaggrin. The expression pattern of involucrin, a protein component of the cornified envelope was altered in a manner similar to that observed with filaggrin. Involucrin expression was evident in many basal keratinocytes in TCDD-treated cultures, a phenomenon never observed in control cultures where involucrin is found only in suprabasal cells. The more basal-proximal expression of filaggrin and involucrin proteins in TCDD-treated samples, like the morphological changes observed at the electron microscope level, indicates a compression of the spinous layer due to TCDD treatment. Additionally, irregular distribution of the membrane-associated differentiation marker transglutaminase-1 was found in some TCDD-treated cultures. Instead of staining in a crisp, contiguous ring at the cell membrane, as in control samples, the staining pattern of transglutaminase-1 in TCDD-treated cultures is somewhat irregular and disrupted at the cell membrane. Keratin 1 expression appears unaltered by TCDD treatment. The overall enhanced differentiation is consistent with the initial histological observation that TCDD-treated organotypic cultures produce a cornified layer earlier than do controls.

3. TCDD Does Not Cause a Change in BrdU Uptake in Keratinocytes in Organotypic Culture Tissue homeostasis in skin relies on the balance among differentiation, proliferation, and death. In order to assess whether the accelerated differentiation we observed in TCDD-treated organotypic cultures is the result of an increase in the rate of proliferation or apoptosis, we performed BrdU uptake experiments, in situ DNA 3' end labeling, and immunohistochemical analysis for active caspase-3. We first sought to determine whether the accelerated differentiation observed could be attributed to changes in proliferation. At 8 days post-plating, TCDD-treated and control (DMSO-treated) organotypic cultures were given 10 µg/ml BrdU in the media 8 hours prior to harvesting. After harvesting, cultures were paraffin embedded, sectioned and stained with an anti-BrdU antibody. The number of BrdU-positive nuclei was calculated as a percent of the total number of nuclei. The number of BrdU positive nuclei ranged from 8% to 15%, but was not significantly different between TCDD-treated and control groups. A t-test analysis of the difference in percent BrdU positive nuclei between treatment and control groups gave a p-value of 0.9186 at a 95% confidence level.

4. TCDD Does Not Induce Apoptosis in Keratinocytes in Organotypic Culture

Apotosis is known to be involved in the modulation of both health and disease states in the skin and its appendages indicating that keratinocytes are fully equipped to initiate an apoptotic cascade in response to a variety of endogenous and exogenous stimuli. Haake, A. R. and R. R. Polakowska, *J. Invest Dermatol* 101: 107–12 (1993); Raskin, C. A., *J. Am Acad Dermatol* 36: 885–98 (1997). Biochemical analysis of keratinocytes has verified their ability to express functional caspases, the proteases responsible for regulating and executing the orderly breakdown of cellular structures observed during apoptosis. Weil, M. et al., *Curr Biol* 9: 361–4 (1999). Some researchers have suggested that keratinocyte terminal differentiation is a specialized form of apoptosis, however, recent studies have indicated that the two events are distinct instead of being interdependent. Gandarillas, A. et al., *Exp Dermatol* 8: 71–9 (1999); Mitra, R. S. et al., *Lab Invest* 76: 99–107 (1997); Weil, M. et al., *Curr Biol* 9: 361–4 (1999).

In situ DNA fragments were detected using TUNEL labeling. Sections from both treatment and control groups (negative control group was treated with DMSO and positive control group was treated with cycloheximide), harvested 8 days post-plating, were prepared according to the manufacturer's protocol. Cycloheximide-treated positive controls displayed numerous positive nuclei in the basal, immediately suprabasal, and cornified layers. Those nuclei detected as positive by 3' DNA end-labeling also displayed morphological characteristics of apoptosis, seen by Hoechst counterstaining. In contrast, both TCDD-treated and vehicle controls showed a negligible amount of labeled cells in all cell layers except the cornified layer. Immunohistochemical analysis for active caspase-3 showed very faint staining in the spinous and granular layers, with no increased staining in TCDD-treated cultures. We therefore conclude that TCDD treatment does not aberrantly induce apoptosis in keratinocytes. These data strongly suggest that accelerated differentiation observed in TCDD-treated organotypic cultures is due to a change in a differentiation-specific pathway, which does not overlap with apoptotic pathways.

TABLE 1

Chromosomal aberrations with passage
Chromosomal analysis was done on 20 spreads of the parental BC-1-Ep at passage 3 and the BC-1-Ep/SL cells at passages 31 and 54

| Passage # | Spreads | 46,XY | 47,XY + i(8q) | 48,XY + i(8q) + i(8q) | 48,XY + i(8q) + i(8q) mar | 49,XY + i(1q) + i(8q) + mar |
|---|---|---|---|---|---|---|
| 3 | 20 | 20 | 0 | 0 | 0 | 0 |
| 31 | 20 | 0 | 20 | 0 | 0 | 0 |
| 54 | 20 | 0 | 17 | 1 | 1 | 1 |

TABLE 2

Tumorigenicity of BC-1-Ep/SL cells in nude mice
To determine if BC-1-Ep/SL cells formed tumors, cells were injected subcutaneously into the flanks of six nude mice at 5 × 10⁶ cells/100 µl F12. For a negative control, BC-1-Ep 6° were injected into the flanks of six nude mice at 3 × 10⁶ cells/100 µl F12. For a positive control, SCC4Y 20° were injected into the flanks of four nude mice. Mice were weighed and tumors measured 20 days later. The injection strategy is shown below.

| Animal # | Condition | Body Weight (gm) | Area of tumor (mm³) |
|---|---|---|---|
| 1 | left flank = BC-1-Ep 6° | 22 | — |
|   | right = BC-1-Ep/SL 35° |   | — |
| 2 | left = BC-1-Ep 6° | 24 | — |
|   | right = BC-1-Ep/SL 35° |   | — |
| 3 | left = SCC4y 20° | 21 | 105.2 |
|   | right = BC-1-Ep/SL 35° |   | — |
| 4 | left = BC-1-Ep 6° | 25 | — |
|   | right = SCC4y 20° |   | 1183.6 |
| 5 | left flank = BC-1-Ep 6° | 23 | — |
|   | right = BC-1-Ep/SL 35° |   | — |
| 6 | left = BC-1-Ep 6° | 22 | — |
|   | right = BC-1-Ep/SL 35° |   | — |
| 7 | left = SCC4y 20° | 22 | 51.3 |
|   | right = BC-1-Ep/SL 35° |   | — |
| 8 | left = BC-1-Ep 6° | 19 | — |
|   | right = SCC4y 20° |   | 463.3 |

TABLE 3

Formulation of cornified envelopes in BC-1-Ep/SL cells
BC-1-Ep/SL cells were grown in the presence of a 3T3 feeder layer. Feeders were removed and 2–3* days later, cells were suspended for 24 hours at ~10⁶/ml in 3F12:1DME + penicillin/streptomycin made semisolid with 1.68% methylcellulose. Adherent cells were rinsed and incubated 24 hours in 3F12:1DME + penicillin/streptomycin. Envelopes were isolated by boiling the cells for 5 minutes in PBS containing 1% SDS and 20 mM DTT, and counted using a hemacytometer.

|  | Treatment | Adherent | Suspended |
|---|---|---|---|
| Exp. 1 | Parent (*4°) | 1.51% | 43.3% |
|  | BC-1-EpSL (31") | 1.32% | 69.8% |
| Exp. 2 | Parent (6°) | 1.79% | 32.8% |
|  | BC-1-EpSL (33") | 1.05% | 73.7% |

TABLE 4

DNA Concentration Impacts on Transient Transfection Efficiency in BC-1-Ep/SL Cells
BC-1-Ep/SL cells were transfected with the GFP containing plasmid pGreenLantern (Gibco) and pcDNA3neo (Invitrogen) with the various amounts of DNA depicted below. The ratio of DNA to GeneFECTOR was kept constant at 1:4. Transfection efficiency was obtained using FACS. Cell number was determined by trypsinization and counting of keratinocytes using a hemacytometer.

| DNA concentration | Aug. 26, 1997 % GFP + Cells | Dec. 16, 1997 % GFP + Cells | Dec, 22, 1997 % GFP + Cells |
|---|---|---|---|
| 15 µg pGL + 5 µg pcDNA3 | 3.79% | 13.64% | 9.88% |
| 20 µg pGL + 6.7 µg pcDNA3 | 3.2% | 5.25% | 8.85% |
| 25 µg pGL + 8.3 µg pcDNA3 | 1.98% | 12.49% | 3.33% |
| Cell Confluence | 70% | 35–40% | 35–40% |

TABLE 5

Ratio of DNA to GeneFECTOR Affects Transient Transfection Efficiency
BC-1-Ep/SL cells were transfected with varying ratios of plasmid DNA (pGL + pcDNA3neo) to transfection reagent (GeneFECTOR). The DNA concentration was held constant at 15 µg of pGreenLantern and 5 µg of pcDNA3neo. Transfection efficiency was obtained using FACS. Cell number was determined by cell trypsinization and hemacytometer counting.

| Ratio of DNA to Genefector | Jan. 30, 1998 % GFP + Cells | Feb. 20, 1998 % GFP + Cells | Feb. 20, 1998 % GFP + Cells |
|---|---|---|---|
| 1:2 | 4.74% | 15.2% | 6.94% |
| 1:3 | 7.23% | 17.54% | 19.36% |
| 1:4 | 3.3% | 7.95% | 16.99% |
| Cell Confluence | 50% | 30% | 30% |

TABLE 6

Stable Transfection of BC-1-Ep/SL Cells Using pGreenLantern
BC-1-Ep/SL cells were transfected with pGreenLantern and pcDNA3 using potimal transient transfection parameters. Twenty-four hours post-transfection, keratinocytes were suspended at a density of 4–6 × 10⁶/ml and stained with 5 mg/ml propidium iodide. BC-1-Ep/SL cells were sterile sorted into four categories based on the fluorescent intensity of GFP. Colony forming efficiency was calculated by counting the number of colonies formed from one thousand cells plated per p60. GFP-positive colonies were counted using an inverted fluorescent microscope with a GFP short pass filter. This table represents one cell sorting experiment.

| Fluorescent Intensity of GFP | Events Sorted | Colony Forming Efficiency | Total Colonies Formed | GFP + Colonies | % GFP + Colony Formers |
|---|---|---|---|---|---|
| Brightest | 63,375 | 0.13% | 83 | 0 | 0% |
| Brights | 54,802 | 0.38% | 208 | 4 | 1.9% |
| Dims | 37,161 | 0.86% | 319 | 6 | 1.9% |
| Dimmest | 62,432 | 0.34% | 212 | 2 | 0.9% |
|  |  |  |  | Total | 4.7% |

TABLE 7

Ratio of thickness of the keratinized layer to non-keratinized layers of organotypic cultures as measured by electron microscopy.

|  | Day 8 | Day 11 |
|---|---|---|
| DMSO | 0.20 (±0.03) | 0.57 (±0.18) |
| TCDD | 0.28 (±0.06) | 1.6 (±0.28) |

We claim:

1. A method for examining the effect of a test factor on reconstructed epidermis, comprising the steps of:
   providing a human stratified squamous epithelial cell culture, wherein the culture comprises spontaneously immortalized human keratinocytes and forms a reconstructed epidermis, wherein the cell culture originated with ATCC CRL 12191;
   exposing the reconstructed epidermis to the factor; and
   evaluating the effect of the factor on the reconstructed epidermis.

2. The method of claim 1, wherein the spontaneously immortalized human keratinocytes are ATCC CRL-12191 cells.

3. The method of claim 1, wherein the spontaneously immortalized human keratinocytes carry an exogenous gene.

4. The method of claim 3, wherein the transgene is green fluorescence protein gene.

5. The method of claim 1, wherein the factor is a material that may contact human skin.

6. The method of claim 5, wherein the material is selected from the group consisting of compounds and mixture of compounds.

7. The method of claim 6, wherein the compound is selected from the group consisting of therapeutics, cosmeceuticals or cosmetic skin products.

8. The method of claim 6, wherein the mixture of compounds is selected from the group consisting of therapeutics, cosmeceutical products or cosmetic skin products.

9. The method of claim 5, wherein the material is selected from the group consisting of inorganic acids, organic acids, acid mixtures, acid derivatives, amines, inorganic bases, organic bases, base mixtures, a mixture of an acid and a base, cleaners, detergents, surfactants, and industrial chemicals.

10. The method of claim 1, wherein the factor is selected from the group consisting of UV light, radiation, air pressure, environment temperature and friction.

11. The method of claim 1, wherein the effect is selected from the group consisting of cell differentiation, cell proliferation, cell survival, cell damage and cell death.

12. The method of claim 1, wherein the effect is selected from the group consisting of tissue culture morphology change, barrier function and tissue strength.

13. The method of claim 1, wherein the effect is toxicity.

14. The method of claim 1, wherein the culture further comprises a base layer of collagen and fibroblasts.

15. The method of claim 1, wherein the factor is in liquid form and is exposed to the reconstructed epidermis as a liquid.

16. The method of claim 1, wherein the factor is in solid form and is exposed to the, reconstructed epidermis as a solid.

17. The method of claim 1, wherein the factor is in emulsion form and is exposed to the epidermis as an emulsion.

18. The method of claim 1, wherein the factor is combined with a solvent and exposed to the reconstructed epidermis as a solvent/factor combination.

19. The method of claim 1, wherein the agent being screened is in liquid form and is exposed to the reconstructed epidermis as a liquid.

20. The method of claim 1, wherein the agent being screened is in solid form and is exposed to the reconstructed epidermis of the solid.

21. The method of claim 1, wherein the agent being screened is an emulsion and is exposed to the reconstructed epidermis as an emulsion.

22. The method of claim 1, wherein the agent being screened is combined with the solvent and is exposed to the reconstructed epidermis as a solvent/agent combination.

23. The method of claim 1, wherein the evaluating comprises microscopic analysis of the reconstructed epidermis.

24. The method of claim 1, wherein the evaluating comprises a histological examination of the reconstructed epidermis.

25. The method of claim 1, wherein the evaluating comprises a visual examination of the reconstructed epidermis.

26. The method of claim 1, wherein the evaluating comprises cell viability analysis.

27. A method for selecting preventive or therapeutic agents for skin damage or benefits caused by a factor, comprising the steps of:

providing a human stratified squamous epithelial cell culture, wherein the culture comprises spontaneously immortalized human keratinocytes and forms a reconstructed epidermis, wherein the cell culture originated with ATCC CRL 12191;

exposing the reconstructed epidermis to a factor;

exposing the reconstructed epidermis to an agent being screened for preventive or therapeutic use; and evaluating the effect of the agent on the reconstructed epidermis and selecting agents that have a preventative or therapeutic effect on epidermis damage or benefits caused by the factor.

28. The method of claim 27, wherein exposing the reconstructed epidermis to the factor occurs prior to exposing the reconstructed epidermis to an agent being screened for preventive or therapeutic use.

29. The method of claim 27, wherein exposing the reconstructed epidermis to the factor occurs after exposing the reconstructed epidermis to an agent being screened for preventive or therapeutic use.

30. The method of claim 27, wherein exposing the reconstructed epidermis to the factor and exposing the reconstructed epidermis to an agent being screened for preventive or therapeutic use occur at the same time.

31. The method of claim 27, wherein the factor is in liquid form and is exposed to the reconstructed epidermis as a liquid.

32. The method of claim 27, wherein the factor is in solid form and is exposed to the reconstructive epidermis as a solid.

33. The method of claim 27, wherein the factor is in emulsion form and is exposed to the epidermis as an emulsion.

34. The method of claim 27, wherein the factor is combined with a solvent and exposed to the reconstructed epidermis as a solvent/factor combination.

35. The method of claim 27, wherein the agent being screened is in liquid form and is exposed to the reconstructed epidermis as a liquid.

36. The method of claim 27, wherein the agent being screened is in solid form and is exposed to the reconstructed epidermis as a solid.

37. The method of claim 27, wherein the agent being screened is an emulsion and is exposed to the reconstructed epidermis as an emulsion.

38. The method of claim 27, wherein the agent being screened is combined with the solvent and is exposed to the reconstructed epidermis as a solvent/agent combination.

39. The method of claim 27, wherein the evaluating comprises microscopic analysis of the reconstructed epidermis.

40. The method of claim 27, wherein the evaluating comprises a histological examination of the reconstructed epidermis.

41. The method of claim 27, wherein the evaluating comprises a visual examination of the reconstructed epidermis.

42. The method of claim 27, wherein the evaluating comprises cell viability analysis.

43. A method of evaluating the effects of a plurality of compounds on human keratinocyte cell cultures comprising:

(a) providing a plurality of cell cultures comprising spontaneously immortalized human keratinocytes, wherein the cultures originated with ATCC CRL 12191, and a set of test compounds;

(b) sequentially exposing said plurality of cell cultures to said set of compounds alone or in combination; and (c) evaluating the effects of said set of compounds on said cell cultures.

44. The method of claim 43, wherein said cell cultures are provided in format selected from the group consisting of 24 well plates and 96 well plates.

45. The method of claim 43, wherein said set of compounds is combinatorial library of compounds.

46. The method of claim 43, wherein said spontaneously immortalized human keratinocytes comprise a reporter gene.

47. The method of claim 46, wherein said reporter gene is GFP.

* * * * *

UNITED STATES PATENT AND TRADEMARK OFFICE
CERTIFICATE OF CORRECTION

PATENT NO. : 6,514,711 B2
DATED : February 4, 2003
INVENTOR(S) : B. Lynn Allen-Hoffmann It is certified that error appears in the above-identified patent and that said Letters Patent is hereby corrected as shown below:

Column 4,
Line 22, ""In the examples below," delete quotation marks before "In." should read -- In the examples below. --

Column 5,
Line 35, "Free steroids" should read -- Free sterois --.
Line 36, "steroid sulfatase," should read -- stoid sulfatase. --
Line 44, "Dermnaphase" should read -- Dermaphase --.

Column 12,
Line 59, "4x10(16)" should read -- 4x10(-16) --.

Column 15,
Line 17, "BC-1-EP 50 degrees" should read -- BC-1-EP 5 degrees --.

Column 25,
Line 17, no comma between "the, reconstructed."

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,514,711 B2                                          Page 1 of 1
DATED         : February 4, 2003
INVENTOR(S)   : B. Lynn Allen-Hoffmann It is certified that error appears in the above-identified patent and that said Letters Patent is hereby corrected as shown below:

Column 4,
Line 22, ""In the examples below," delete quotation marks before "In." should read -- In the examples below. --

Column 5,
Line 44, "Dermnaphase" should read -- Dermaphase --.

Column 12,
Line 59, "4x10(16)" should read -- 4x10(-16) --.

Column 15,
Line 17, "BC-1-EP 50 degrees" should read -- BC-1-EP 5 degrees --.

Column 25,
Line 17, no comma between "the, reconstructed."

This certificate supersedes Certificate of Correction issued May 13, 2003.

Signed and Sealed this

Second Day of December, 2003

JAMES E. ROGAN
*Director of the United States Patent and Trademark Office*